United States Patent [19]

Gaitanopoulos et al.

[11] Patent Number: 4,600,714
[45] Date of Patent: Jul. 15, 1986

[54] FENOLDOPAM 4',8-BIS-HYDROGEN SULFATE AND DOPAMINERGIC USE THEREOF

[75] Inventors: Dimitri Gaitanopoulos, Eagleville; Joseph Weinstock, Phoenixville, both of Pa.

[73] Assignee: SmithKline Beckman Corporation, Philadelphia, Pa.

[21] Appl. No.: 604,101

[22] Filed: Apr. 26, 1984

[51] Int. Cl.$^4$ .................... A61K 31/59; C07D 223/14
[52] U.S. Cl. .............................. 514/213; 260/239 BB
[58] Field of Search .................. 260/239 BB; 514/213

[56] References Cited

U.S. PATENT DOCUMENTS 4,388,240  6/1983  Dewey et al. ................ 260/239 BB

FOREIGN PATENT DOCUMENTS 0022330  6/1980  European Pat. Off. .

*Primary Examiner*—Glennon H. Hollrah
*Assistant Examiner*—D. B. Springer
*Attorney, Agent, or Firm*—Vincent L. Fabiano; Stuart R. Suter; Alan D. Lourie

[57] ABSTRACT

Fenoldopam 4',8-bis-hydrogen sulfate and its salts are useful prodrugs to obtain extended dopaminergic activity. A useful species is the monoammonium salt.

7 Claims, No Drawings

FENOLDOPAM 4′,8-BIS-HYDROGEN SULFATE AND DOPAMINERGIC USE THEREOF

This invention concerns new sulfate derivatives of the renal dopaminergic agent, fenoldopam. More specifically, the compounds of this invention are 6-chloro-7,8-dihydroxy-1-(4′-hydroxyphenyl)-2,3,4,5-tetrahydro-1H-3-benzazepin, 4′,8-bis-hydrogen sulfate and its pharmaceutically acceptable salts.

DESCRIPTION OF THE PRIOR ART

U.S. Pat. No. 4,388,240 describes the preparation and isolation of three monosulfate esters of fenoldopam. No mention is made of any disulfate esters.

DESCRIPTION OF THE INVENTION

The compounds of this invention have the following structural formula:

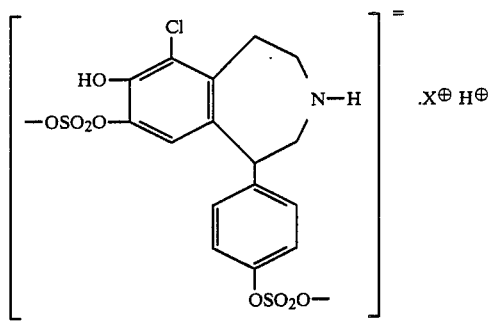

in which $X^{\oplus}$ is $H^{\oplus}$ or a pharmaceutically acceptable cation. The monoammonium salt is preferred.

The ammonium salt of the compounds of this invention (formula I in which $X^{\oplus}$ is $NH_4^{\oplus}$) is prepared by O-esterification of fenoldopam using a 50% excess of sulfur trioxide pyridine complex ($Py.SO_3$) in a mixture of dry pyridine and dimethylformamide. The syrupy reaction mixture from the sulfation is purified using preparative high performance liquid chromatography over a $C_{18}$ reverse phase column using a mobile phase of 12% methanol/88% 0.05 N ammonium acetate buffer. The first fraction eluted from the column contains the 4′,8-bis-hydrogen sulfate as the monoammonium salt.

The ammonium salt of formula I is stable when purified but, upon neutralization, it slowly disproportionates into the 4′ and 8-monosulfate esters of fenoldopam and fenoldopam itself. The free dibasic disulfate ester is prepared during the sulfation reaction and is converted to its relatively stable salt form during the work-up of the reaction mixture. The parent bis-hydrogen sulfate was not isolated.

The compounds of this invention are useful as a long-acting prodrug of fenoldopam, especially for parenteral use. In the anesthetized renal dog protocol, which is described in detail in U.S. Pat. No. 4,197,297, ammonium salt (formula 1 in which $X^{\oplus}$ is $NH_4^{\oplus}$) had a renal vascular resistance $ED_{15}$ of 69 μg/kg during the test period of intravenous infusion but a potent 100% increase in renal blood flow was observed over a lengthy post drug period. The renal dopaminergic activity lasted for two hours without a significant change in heart rate or blood pressure.

While the mono-8-sulfate ester of fenoldopam had an $ED_{15}$ of 19 μg/kg in this test, no drug effect was observed in the post-drug period of the protocol.

The salts of formula I are particularly useful to prepare parenteral products which produce biological utilities similar to those of the parent compound but over an extended period. Exemplary of the uses of the compounds are for treatment of hypertension or severe kidney dysfunction. The compounds of this invention are administered intravenously by infusion using an effective, nontoxic dose selected from the range of 0.02–1.5 mcg/kg/min for a human patient of average weight. An effective dosage unit of from 5–35 mg is administered from 1–5 times daily for intramuscular use.

Pharmaceutical dosage unit preparatives are prepared using extenders such as mannitol, preservatives or inert buffers to maintain isotonic properties. Freeze dried or sterile dispersible powders in pouches, dosage unit ampoules or multidose vials are typical parenteral carrier forms. These are administered intravenously or intramuscularly as needed to induce an antihypertensive effect in a human patient in need thereof. Oral dosage units containing from 75–500 mg of the ester combined with a solid carrier in the form of a capsule, tablet or the like are prepared by methods known to the art. These are administered from 1–3 times daily to a patient in need of dopaminergic treatment.

Other pharmaceutically acceptable salts are included in this invention. Certain alkali metal, alkaline earth metal or organic amine salts are known to the art to be so used. These are prepared as described herein, by forming the mono-salt prior to purification. Among the cations of this group ($X^{\oplus}$ of formula 1) are sodium or potassium. It should be noted that one acid group is usually internally neutralized by the basic center at position 3.

Also included in this invention are the bis-hydrogen sulfate esters of separated optical isomers of fenoldopam, especially of the R-isomer. These are prepared as described herein using, as starting materials, the isomers which are prepared as described in the art.

The following example is intended to illustrate this invention. All temperatures are Centigrade.

EXAMPLE 1

Sulfur trioxide pyridine complex

Chlorosulfonic acid (3.0 ml, 0.0454 mol, 150 M %) was added slowly to a solution of dry pyridine (9.84 ml, 0.121 mol) in dry dimethylformamide (60 ml) which had been cooled to −10°. The resulting clear solution was stirred for 10 minutes at room temperature.

O-Sulfation of fenoldopam

The freshly prepared pyridine complex solution was added all at once to a stirred solution of fenoldopam as the methane sulfonate salt (12.06 g, 0.030 mol, 100 M %) in dry pyridine (180 ml). The mixture was stirred for 0.5 hours at room temperature, then, heated on a steam bath for 0.5 hours. The resulting dark amber solution was chilled for 0.5 hours at −10°, filtered to remove pyridinium salts, transferred into a tared 1-necked, 2-L, round bottom flask and evaporated on a Buchi rotavap. At 70°, at reduced pressure, the excess pyridine complex began to sublime (0.5 hr) and a syrupy residue was formed. At this point, the cold-traps were cleaned and the syrupy residue was rotavaped at 70°, at reduced pressure, for 45 minutes to remove most of the volatiles, thereby leaving 23.83 g of syrup. The syrup should weigh no more than 26.91 g—the theoretical weight of the total solid content of the reaction mixture.

The syrup was dissolved in 90 ml of mobile phase (MP) [12% methanol, 88% buffer (0.05 N ammonium acetate, pH 4)]. The flask was scratched to induce crystallization, then, left standing at room temperature for 3 hours. The resulting crystalline solid was filtered, washed with 50 ml of the mobile phase mixture and dried to give 6.41 g of solid which is mostly 4'-sulfate. The combined filtrate and washing (140 ml) contains 7.0 g of 0-sulfates and traces of fenoldopam. The pH is adjusted to pH 3.4–4.0 with hydrochloric acid or aqueous ammonia as needed.

Chromatography

The partially purified reaction mixture was further purified by preparative reverse phase high performance liquid chromatography (HPLC).

| Preparative HPLC | |
|---|---|
| Apparatus: | JY-100 CHROMATOSPAC |
| Column: | 40 mm × 45 cm |
| Solid Phase (SP): | Whatman, Partisil 40 ODS-3 (192 g) length 37 cm (Lot #100627) |
| Mobile Phase (MP): | 12% methanol 88% buffer (0.05 N NH4OAc, pH 4) |
| Flow Rate: | 50 ml/min |
| Pressure: | 2.0 bar |
| Detector: | GOW-MAC 80-850 LC/LV preparative detector 280 nm |
| Attenuation: | AUFS 0.64 |

The sample (140 ml) was injected at 5–10 ml/min. Then, the flow rate was adjusted to 50 ml/min.

The first fraction, containing the 4',8-bis ester, eluted between 18 and 26 min (k'=3.46) (500 ml); 4'-SO3 eluted between 38 and 48 min (k'=6.88) (700 ml); and the fraction containing 7-SO3/8-SO3 (23:75%) mixture eluted between 60–85 min (k'=11.50) (1000–1400 ml).

Isolation of fenoldopam 4',8-bis-hydrogen sulfate

The 4',8-bis-hydrogen sulfate was purified by concentrating the designated fraction on a rotavap at 50°, aspirator pressure, then lyophilizing. The resulting solid residue crystallized as the ammonium salt upon trituration with methanol. The product was washed with methanol and air dried to give an analytically pure ammonium hydrate of fenoldopam 4',8-bis-hydrogen sulfate, mp, 160° softens, 180° melts, 185° resolidifies, 200°–205° dec.

Analytical

The preparative reactions and chromatographic fractions were analyzed by analytical HPLC.

| Column: | WHATMAN, Partisil 5 ODS-3 RAC II-10 |
|---|---|
| Mobile Phase: | same as preparative HPLC |
| Flow Rate: | 2 mil/min |
| Pressure: | 13.8 × 10$^{-6}$ Pa |
| Detector: | 275 nm |

| Compound | Retention (min) | k' |
|---|---|---|
| 4',8-diSO3 | 2.63 | 3.46 |
| 4'-SO3 | 3.93 | 5.66 |
| 7-SO3 | 6.16 | 9.44 |
| 8-SO3 | 6.88 | 10.66 |
| fenoldopam | 7.83 | 12.27 |

Anal. Calcd. for $C_{16}H_{16}ClNO_9S_2 \cdot NH_3 \cdot 2.5\ H_2O$: C, 36.40; H, 4.58; N, 5.31. Found: C, 37.00; H, 4.40; N, 5.30.

What is claimed is:

1. A compound of the formula:

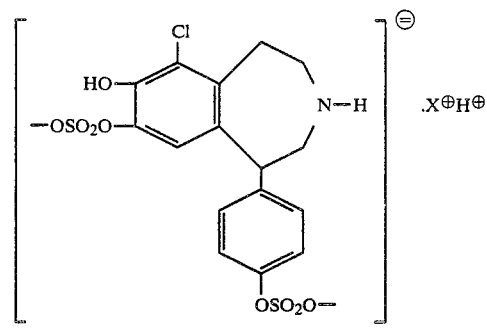

in which $X^{\oplus}$ is $H^{\oplus}$ or a pharmaceutically acceptable cation.

2. The compound of claim 1 in which $X^{\oplus}$ is $Na^{\oplus}$ or $K^{\oplus}$.

3. The compound of claim 1 which is 6-chloro-7,8-dihydroxy-1-(4'-hydroxyphenyl)-2,3,4,5-tetrahydro-1H-3-benzazepine, 4',8-bis-hydrogen sulfate, ammonium salt.

4. The compound of claim 1 which is 6-chloro-7,8-dihydroxy-1-(4'-hydroxyphenyl)-2,3,4,5-tetrahydro-1H-3-benzazepine, 4',8-bis-hydrogen sulfate.

5. A pharmaceutical composition having renal dopaminergic activity comprising an effective therefor, nontoxic quantity of a compound of claim 1 and a pharmaceutical carrier.

6. The composition of claim 4 in which the composition is adapted for parenteral use.

7. The method of inducing dopaminergic activity in a patient in need thereof comprising administering orally or parenterally to said patient an effective therefor, nontoxic quantity of a compound of claim 1.

* * * * *